(12) United States Patent
Lovell

(10) Patent No.: US 6,660,751 B1
(45) Date of Patent: Dec. 9, 2003

(54) SULFONAMIDE DERIVATIVES AS 5-HT$_7$ RECEPTOR ANTAGONISTS

(75) Inventor: Peter John Lovell, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/937,043

(22) PCT Filed: Mar. 14, 2000

(86) PCT No.: PCT/EP00/02267

§ 371 (c)(1),
(2), (4) Date: Sep. 20, 2001

(87) PCT Pub. No.: WO00/56712

PCT Pub. Date: Sep. 28, 2000

(30) Foreign Application Priority Data

Mar. 23, 1999 (GB) .............................................. 9906624

(51) Int. Cl.[7] .................... C07D 401/04; C07D 401/12; C07D 401/14; A61K 31/4523; A61P 25/24
(52) U.S. Cl. ....................... 514/321; 546/198; 546/199; 546/271.7; 546/273.4; 514/322; 514/338
(58) Field of Search ................ 546/199, 198, 546/271.7, 273.4; 514/321, 322, 338

(56) References Cited

FOREIGN PATENT DOCUMENTS

| FR | 2 675 801 | 10/1992 |
|---|---|---|
| GB | WO 97 29097 | 8/1997 |
| GB | WO 97 49695 | 12/1997 |

OTHER PUBLICATIONS

Malleron J., et al. "New Indole Derivatives as Potent and Selective Serotonin Uptake Inhibitors", Journal of Medicinal Chemistry, US,, American Chemical Society. Washington vol. 36, No. 9, 1993, pp. 1194–1202, XP000195950 ISSN: 0022–2623.

*Primary Examiner*—Mark L. Berch
*Assistant Examiner*—Kahsay Habte

(74) *Attorney, Agent, or Firm*—Soma G. Simon; Mary E. McCarthy; Charles M. Kinzig

(57) ABSTRACT

The invention relates to novel sulfonamide compounds having 5-HT$_7$ receptor antagonist activity, processes for their preparation, to compositions containing them and to their use in the treatment of CNS and other disorders.

(I)

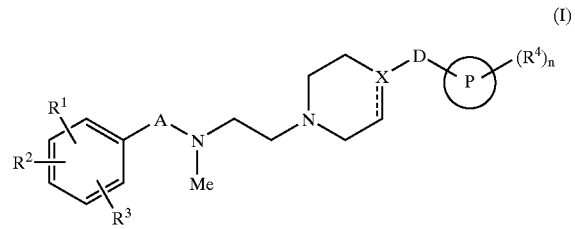

wherein:

Q is phenyl or thienyl;

$R^1$ is halogen, hydroxy, $C_{1-6}$alkyl, $CF_3$, $OCF_3$ or $C_{1-6}$alkoxy;

m is 0, 1, 2 or 3;

$R^2$ is $C_{1-4}$alkyl;

X is carbon or CH,

=== is a single bond when X is nitrogen or CH or

=== is a double bond when X is carbon,

D is a single bond, C=O, O or $CH_2$ subject to the proviso that when X is nitrogen then D is not oxygen;

P is a 5 or 6 membered heteroaryl ring containing 1 to 3 heteroatoms selected from oxygen, nitrogen and sulphur, or a benzofused heteroaryl ring containing 1 to 3 heteroatoms selected from oxygen, nitrogen and sulphur;

$R^3$ is $C_{1-6}$alkyl optionally substituted by $NR^4R^5$, aryl, aryl$C_{1-6}$alkyl, $C_{1-6}$alkoxy, $C_{1-6}$alkylthio, cyano, hydroxy, nitro, halogen, $CF_3$, $C_2F_5$, $NR^4R^5$, $CONR^4R^5$, $NR^4COR^5$, $S(O)_pNR^4R^5$, CHO, $OCF_3$, $SCF_3$, $CH_2OR^6$, $CO_2R^6$ or $COR^6$ where p is 0, 1 or 2 and $R^4$, $R^5$ and $R^6$ are independently hydrogen, $C_{1-6}$alkyl, aryl or aryl$C_{1-6}$alkyl;

n is 0, 1, 2 or 3.

9 Claims, No Drawings

SULFONAMIDE DERIVATIVES AS 5-HT₇ RECEPTOR ANTAGONISTS

This invention relates to novel sulfonamide compounds having pharmacological activity, processes for their preparation, to compositions containing them and to their use in the treatment of CNS and other disorders.

WO 97/29097, WO 98/48681 and WO 97/49695 all disclose a series of sulfonamide derivatives that are 5-HT₇ receptor antagonists and are useful in the treatment of various CNS diseases. Malleron et al (J. Med. Chem., 1993, 36, 1194–1202) discloses a series of indole derivatives that are claimed to act as potent and selective serotonin uptake inhibitors.

A structurally novel class of compounds has now been found which also possess 5-HT₇ receptor antagonist activity. The present invention therefore provides, in a first aspect, a compound of formula (I) or a pharmaceutically acceptable salt thereof:

(I)

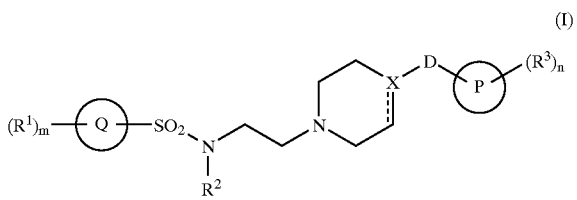

wherein:
Q is phenyl or thienyl;
$R^1$ is halogen, hydroxy, $C_{1-6}$alkyl, $CF_3$, $OCF_3$ or $C_{1-6}$alkoxy;
m is 0, 1, 2 or 3;
$R^2$ is $C_{1-4}$alkyl;
X is nitrogen, carbon or CH,
=== is a single bond when X is nitrogen or CH or
=== is a double bond when X is carbon;
D is a single bond, C=O, O or $CH_2$ subject to the proviso that when X is nitrogen then D is not oxygen;
P is phenyl, naphthyl, a 5 or 6 membered heteroaryl ring containing 1 to 3 heteroatoms selected from oxygen, nitrogen and sulphur, or a benzofused heteroaryl ring containing 1 to 3 heteroatoms selected from oxygen, nitrogen and sulphur;
$R^3$ is $C_{1-6}$alkyl optionally substituted by $NR^4R^5$, aryl, aryl$C_{1-6}$alkyl, $C_{1-6}$alkoxy, $C_{1-6}$alkylthio, cyano, hydroxy, nitro, halogen, $CF_3$, $C_2F_5$, $NR^4R^5$, $CONR^4R^5$, $NR^4COR^5$, $S(O)_pNR^4R^5$, CHO, $OCF_3$, $SCF_3$, $CH_2OR^6$, $CO_2R^6$ or $COR^6$ where p is 0, 1 or 2 and $R^4$, $R^5$ and $R^6$ are independently hydrogen, $C_{1-6}$alkyl, aryl or aryl$C_{1-6}$akyl;
n is 0, 1, 2 or 3.

Alkyl groups whether alone or as part of another group may be straight chain or branched. The term 'halogen' is used herein to describe, unless otherwise stated, a group selected from fluorine, chlorine, bromine or iodine. The term 'aryl' is used herein to describe, unless otherwise stated, a group such as phenyl or naphthyl optionally substituted by one or more $C_{1-6}$alkyl or halogen. The term 'naphthyl' is used herein to denote, unless otherwise stated, both naphthalen-1-yl and naphthalen-2-yl groups.

When Q is thienyl a preferred group is thien-2-yl. Preferably Q is phenyl.

When m is 1, $R^1$ is preferably halogen (particularly fluorine or chlorine), a $C_{1-6}$alkyl group (particularly methyl, ethyl, isopropyl or t-butyl), $CF_3$ or $C_{1-6}$alkoxy group (particularly methoxy or ethoxy). When m is 2 or 3 the groups $R^1$ may be the same or different.

When Q=phenyl and m=1 preferred examples include moieties in which $R^1$ is either a fluoro group with a para relationship with respect to the sulfonamide group or is a methyl group with a meta relationship with respect to the sulfonamide linkage. When Q=phenyl and m=2 preferred examples include those in which the $R^1$ groups are independently halogen or $C_{1-6}$alkyl substituted at the 2, 3 or 2, 4 positions with respect to the sulfonamide linkage. When Q=phenyl and m=3 preferred examples include those in which the $R^1$ groups are independently halogen (particularly chloro), $C_{1-6}$alkyl (particularly methyl) or $CF_3$ substituted at the 2, 4 and 5 positions with respect to the sulfonamide linkage.

Suitable examples of $R^2$ groups include methyl, ethyl, isopropyl or n-butyl. Preferably $R^2$ is methyl or isopropyl, most preferably isopropyl.

Preferably X is nitrogen or CH such that === is a single bond. Most preferably X is CH.

Preferably D is a single bond.

When P is a 5 or 6 membered heteroaryl ring suitable examples include thienyl, furyl, pyrrolyl, triazolyl, imidazolyl, oxazolyl, thiazolyl, oxadiazolyl, isothiazolyl, isoxazolyl, thiadiazolyl, pyridyl, pyrimidyl, pyrrolidinyl and pyrazinyl. When P is a benzofused heteroaryl ring suitable examples include indolyl, benzimidazolyl, benzoxazolyl, benzothiazolyl, quinolinyl and isoquinolinyl. The heterocyclic groups listed above can be linked to the remainder of the molecule via a carbon atom or, when present, a suitable nitrogen atom. It will be appreciated however, that when D is O then the heteroaryl ring must be linked to the rest of the molecule via a carbon atom. Preferably P is phenyl, naphthyl, pyrimidin-2-yl or is a benzofused heteroaryl ring selected from the group consisting of quinolin-4yl, 2-oxo-2,3-dihydrobenzimidazol-1-yl, 2-oxo-2,3-dihydrobenzaxazol-1-yl, indol-3-yl, indol-2-yl, benzoxazol-2-yl, benzothiazol-2-yl and particularly benzimidazol-2-yl.

When n is 1, $R^3$ is preferably halogen (particularly fluorine or chlorine), a $C_{1-6}$alkyl optionally substituted by $NR^4R^5$ (particularly methyl), hydroxy, $CF_3$, $C_{1-6}$alkoxy (particularly methoxy) or groups $COR^6$ or $CO_2R^6$ in which $R^6$ is methyl. When n is 2 or 3 the groups $R^3$ may be the same or different. Preferably n is 0 or 1.

Particularly preferred compounds of the invention include:
N-(2-(4-(1H-Benzimidazol-2-yl)-piperidin-1-yl)-ethyl)-3,N-dimethyl benzene sulfonamide,
3,4 Dichloro-N-(2-(4(1H-indol-3-yl)-piperidin-1-yl)-ethyl)-N-methyl-benzene sulfonamide,
2,4,5-Trichloro-N-ethyl-(2-(4-(5-fluoro-1H-benzimidazol-2-yl)-piperidin-1-yl)-ethyl)-benzene sulfonamide,
2,4,5-Trichloro-N-(2-(4-(5-fluoro-1H-benzimidazol-2-yl)-piperidin-1-yl)-ethyl)-N-isopropyl benzene sulfonamide,
4-Chloro-2,5-dimethyl-N-(2-(4-(5-fluoro-1 H-benzimidazol-2-yl)-piperidin-1-yl)-ethyl)-N-isopropyl benzene sulfonamide,
N-(2-(4-(1H-Benzimidazol-2-yl)-piperazin-1-yl)-ethyl)-2,4,5-trichloro-N-isopropyl-benzene-sulfonamide,
3,N-Dimethyl-N-(2-(4-(2-methyl-1H-indol-3-yl)-3,6dihydro-2H-pyridin-1-yl)-ethyl)-benzene sulfonamide,
4-Fluoro-(N-(2-(4-(2-oxo-2,3-dihydro-benzimidazol-1-yl)3,6-dihydro-2H-pyridin-1-yl)ethyl)-benzene sulfonamide, 2,3,4-Trichloro-N-(2-(4-(5-fluoro-1H-benzimidazol-2-yl)-piperidin-1-yl)-ethyl-N-methyl-benzene-sulfonamide, 2,5-Dibromo-N-(2-(4-(5-fluoro-1H-benzimidazol-2-yl)-piperidin-1-yl)-ethyl-N-methyl-benzene-sulfonamide, 2,4-Dichloro-N-(2-(4-(5-fluoro-1H-benzimidazol-2-yl)-piperidin-1-yl)-ethyl-5,N-dimethyl-benzene-sulfonamide, 4,5-Dichloro-N-(2-(4-(5-fluoro-1H-benzimidazol-2-yl)piperidin-1-yl)-ethyl)-N-methyl-2-trifluoromethyl-benzenesulfonamide, 2-Chloro-4-fluoro-N-(2-(4-(5-fluoro-1H-benzimidazol-2-yl)-piperidin-1-yl)-ethyl-N-methyl-benzene-sulfonamide, N-(2-(4-(1H-Benzimidazol-2-yl)-piperazin-1-yl)-ethyl)-3,N-dimethyl benzene sulfonamide, N-2-(4-(1H-Benzimidazol-2-yl)-piperazin-1-yl)-ethyl)-2,4,5-trichloro-N-methyl-benzenesulfonamide, 2,4,5-Trichloro-N-(2-(4-(5-fluoro-1H-benzimidazol-2-yl)piperazin-1-yl)-ethyl)-N-methyl benzene sulfonamide, 4-Fluoro-N-(2-(4-(2-methoxyphenyl)-piperazin-1-yl)-ethyl)-N-methyl benzene sulfonamide N-{2-[4-(1H-Benzimidazol-2-yl)-piperazin-1-yl]-ethyl}-2,4-dichloro-5,N-dimethyl-benzenesulfonamide or a pharmaceutically acceptable salt thereof Other preferred compounds of this invention include those shown in Tables 1–5 below.

The compounds of the formula (I) can form acid addition salts with acids, such as conventional pharmaceutically acceptable acids, for example maleic, hydrochloric, hydrobromic, phosphoric, acetic, futmaric, salicylic, citric, lactic, mandelic, tartaric and methanesulphonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises coupling a compound of formula (II):

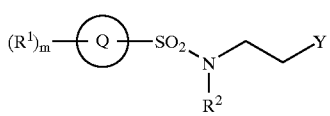

(II)

in which Q, $R^1$, $R^2$ and m are as defined in formula (I) and Y is a leaving group with a compound of formula (III):

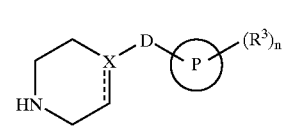

(III)

in which ===, X, D, P, n and $R^3$ are as defined in formula (I);

and optionally thereafter if appropriate:
  removing any protecting groups;
  forming a pharmaceutically acceptable salt.

Suitable leaving groups Y include halogen (particularly chloro) and —$OSO_2Ar$ groups such as tosylate. The reaction of a compounds of formulae (II) and (III) is preferably carried out in a solvent such as acetonitrile or dichloromethane optionally in the presence of sodium iodide and a base such as potassium carbonate.

Those skilled in the art will appreciate that it may be necessary to protect certain groups. Suitable protecting groups and methods for their attachment and removal are conventional in the art of organic chemistry, such as those described in Greene T. W. 'Protective groups in organic synthesis' New York, Wiley (1981).

Compounds of formulae (II) and (III) are either commercially available or are prepared using methods described herein or analogous to known methods.

Pharmaceutically acceptable salts may be prepared conventionally by reaction with the appropriate acid or acid derivative.

Compounds of formula (I) and their pharmaceutically acceptable salts have 5-$HT_7$ receptor antagonist activity and are believed to be of potential use for the treatment or prophylaxis of certain CNS disorders such as anxiety, depression, sleep disorders (including disturbances of Circadian rhythms), migraine, Parkinson's disease, schizophrenia, pain, appetite disorders and other indications such as inflammation, spastic colon, renal disorders, hypotension, cardiovascular shock, stroke, septic shock and gastrointestinal diseases such as IBS (irritable bowel syndrome).

Thus the invention also provides a compound of formula (I) or a pharmaceutically acceptable salt or a solvate thereof, for use as a therapeutic substance, in particular in the treatment or prophylaxis of the above disorders. In particular the invention provides a compound of formula (I) or a pharmaceutically acceptable salt thereof or a solvate thereof for use in the treatment or prophylaxis of depression, migraine and/or sleep disorders.

In another aspect the invention provides the use of a compound of formula (I) or a pharmaceutically acceptable salt or a solvate thereof, for the manufacture of a medicament for the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt or a solvate thereof.

The present invention also provides a pharmaceutical composition, which comprises a compound of formula (I) or a pharmaceutically acceptable salt thereof and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of the compounds of the invention.

DESCRIPTION 1

Toluene-3-sulfonic Acid 2-(Methyl-(toluene-3-sulfonyl)-amino)-ethyl Ester (D1)

To a solution of 2-methylaminoethanol (1.0 g, 13 mmol) and diisopropylethylamine (5.8 ml, 33 mmol) in dichloromethane (50 ml) at room temperature was added 3-methylphenylsulfonyl chloride (5.6 g, 29 mmol). The solution was heated to reflux under argon for 12 hours then cooled and partitioned between saturated aqueous sodium bicarbonate and dichloromethane. The organic phase was dried over sodium sulfate and concentrated in vacuo. The residue was purified by silica gel chromatography to afford the title compound (2.5 g, 50%).

1H NMR (CDCl$_3$) 7.69 (2H, m), 7.55 (2H, m), 7.47 (2H, m), 7.40 (2H, m), 4.19 (2H, t, 5.6 Hz), 3.33 (2H, t, 5.6 Hz), 2.78 (3H, s), 2.46 (3H, s), 2.43 (3H, s).

DESCRIPTION 2

4-Fluorobenzenesulfonic Acid 2-((4-Fluorobenzenesulfonyl)-methyl-amino)-ethyl Ester (D2)

The title compound was prepared from 2-methylamino ethanol and 4-fluorophenyl sulfonyl chloride using the method described in Description 1.

1H NMR (CDCl$_3$) 7.96 (2H, m), 7.80 (2H, m), 7.26 (4H, m), 4.21 (2H, t, 5.6 Hz), 3.34 (2H, t, 5.6 Hz), 2.79 (3H, s).

DESCRIPTION 3

3,4-Dichlorobenzenesulfonic Acid 2-((3,4-Dichlorobenzenesulfonyl)-methyl-amino)-ethyl Ester (D3)

The title compound was prepared from 2-methylamino ethanol and 3,4 dichlorophenyl sulfonylchloride using the method described in Description 1.

1H NMR (CDCl$_3$) 7.86 (1H, m), 7.80 (1H, m), 7.67–7.54 (4H, m), 4.19 (1H, m), 4.37 (1H, m), 3.33 (2H, m), 2.83 (3H, s).

DESCRIPTION 4

2,4,5-Trichlorobenzenesulfonic Acid 2-(Methyl 2,4,5-trichlorobenzenesulfonyl)-amino)-ethyl Ester (D4)

The title compound was prepared from 2-methylamino ethanol and 2,4,5trichlorophenylsulfonylchloride using the method described in Description 1.

1H NMR (DMSO-d$_6$) 8.11 (1H, s), 8.07 (1H, s), 8.05 (1H, s), 7.82 (1H, s), 4.15 (1H, m), 3.71 (1H, m), 3.51 (2H, m), 2.89 (3H, s).

DESCRIPTION 5

2,4,5-Trichloro-N-ethyl-N(2-hydroxyethyl)-benzene Sulfonamide (D5)

The title compound was prepared from 2-ethylamino ethanol and 2,4,5trichlorophenylsulfonylchloride using the method described in Description 1.

1H NMR (CDCl$_3$) 8.20 (1H,.s), 7.63 (1H, s), 3.78 (2H, q, 5.5 Hz), 3.49 (4H, m), 1.93 (1H, t, 5.6 Hz), 1.16 (3H, t, 7.1 Hz).

DESCRIPTION 6

Methane Sulfonic Acid 2-(Ethyl-(2,4,5-trichloro-benzenesulfonyl)-amino) Ethyl Ester (D6)

A solution of D5 (1.2 g, 3.6 mmol) and methanesulfonyl chloride (0.31 mL, 4 mmol) in triethylamine (0.75 mL, 5.4 mmol) and dichloromethane (25 mL) was stirred at room temperature for 4 hrs. The reaction mixture was washed with saturated aqueous sodium bicarbonate, the organic phase dried over sodium sulfate and concentrated in vacuo to afford the title compound which was used in subsequent preparations without further purification. MH+ 410/412/414/416.

DESCRIPTION 7

2,4,5-Trichloro-N-(2-chloroethyl)-N-isopropyl Benzene Sulfonamide (D7)

The title compound was prepared from 2-isopropylamino ethanol and 2,4,5trichlorophenylsulfonylchloride using the method described in Description 1.

1H NMR (CDCl3) 8.22 (1H, s), 7.63 (1H, s), 3.96 (1H, m), 3.61 (4H, m), 1.16 (6H, d, 6.7 Hz).

DESCRIPTION 8

4-Chloro 2,5-dimethylbenzenesulfonic Acid 2-(isopropyl-(4-chloro 2,5-dimethylbenzenesulfonyl)-amino)-ethyl Ester (D8)

The title compound was prepared from 2-isopropylamino ethanol and 4-chloro 2,5-dimethylphenylsulfonylchloride using the method described in Description 1.

1H NMR (DMSO-$d_6$) 8.16 (1H, s), 8.11 (1H, s), 3.80 (2H, t, 5.6 Hz), 3.60 (2H, t, 5.6 Hz), 2.90 (3H, s).

DESCRIPTION 9

2,3,4-Trichloro-N-(2-chloroethyl)-N-methyl Benzene Sulfonamide (D9)

The title compound was prepared from 2-methylamino ethanol and 2,3,4trichlorophenylsulfonylchloride using the method described in Description 1.

DESCRIPTION 10

2,5 Dibromo-N-(2-chloroethyl)-N-methyl Benzene Sulfonamide (D10)

The title compound was prepared from 2-methylamino ethanol and 2,5dibromophenylsulfonylchloride using the method described in Description 1.

DESCRIPTION 11

2,4 Dichloro 5-methyl-N-(2-chloroethyl)-N-methyl Benzene Sulfonamide (D11)

The title compound was prepared from 2-methylamino ethanol and 2,4-dichloro-5-methyl phenylsulfonylchloride using the method described in Description 1.

DESCRIPTION 12

4,5-Dichloro-N-(2-chloroethyl)-N-isopropyl-2-trifluoromethyl-benzenesulfonamide (D12)

The title compound was prepared from 2-isopropylamino ethanol and 4,5-dichloro-2-trifluoromethyl-phenylsulfonyl chloride. MH+ 398/390/392/394.

DESCRIPTION 13

2-Chloro-4-fluoro-N-(2-chloroethyl)-N-methyl Benzene Sulfonamide (D13)

The title compound was prepared from 2-methylamino ethanol and 2-chloro-5-fluoro-phenylsulfonylchloride using the method described in Description 1.

DESCRIPTION 14

4-(1H-Benzimidazol-2-yl)piperidine (D14)

A mixture of 4-piperidine carboxylic acid (5.30 g, 40 mmol), 1,2-diaminobenzene (4.32 g, 40 mmol) and poly-phosphoric acid (40 g) were heated to 190° C. for 14 hours. Cooled, diluted with water (150 ml) and basified with 50% KOH to pH 8. Solution cooled in an ice/salt bath to give a precipitate which was collected by filtration and washed with water. Solid dried in vacuo to afford the title compound (8.0 g, 100%).

1H NMR (CDCl$_3$) 7.48 (2H, m), 7.09 (2H, m), 3.04 (2H, m), 2.92 (2H, m), 2.60 (2H, m), 2.55 (1H, m), 1.95 (2H, m), 1.71 (2H, m). MH+ 202.

DESCRIPTION 15

4-(4-Methyl-1H-benzimidazol-2-yl)piperidine (D15)

The title compound was prepared from isonipecotic acid and 2,3 diamino toluene using the method described in Description 14. MH+ 216.

DESCRIPTION 16

4-(5Methyl-1H-benzimidazol-2-yl)piperidine (D16)

The title compound was prepared from isonipecotic acid and 3,4 diamino toluene using the method described in Description 14. MH+ 216.

DESCRIPTION 17

4-(5-Fluoro 1H-benzimidazol-2-yl)piperidine (D117)

The title compound was prepared from isonipecotic acid and 2,3 diamino fluorobenzene using the method described in Description 14. MH+ 220.

DESCRIPTION 18

4-(5-Hydroxy-1H-benzimidazol-2-yl)piperidine (D18)

The title compound was prepared from isonipecotic acid and 3,4 diamino anisole using the method described in Description 14. MH+ 218.

DESCRIPTION 19

4Benzothiazol-2-yl)piperidine (D19)

The title compound was prepared from isonipecotic acid and 2-aminothiophenol using the method described in Description 14. MH+ 219.

DESCRIPTION 20

4-(Benzoxazol-2-yl)piperidine (D20)

The title compound was prepared from isonipecotic acid and 2-aminophenol using the method described in Description 14. MH+ 203.

DESCRIPTION 21

N-(2-(4-Benzylpiperazin-1-yl)-ethyl)-3,N-dimethyl Benzene Sulfonamide (D21)

A solution of D1 (22 g, 89 mmol) and N-benzylpiperazine (15.7 g, 89 mmol) was heated to reflux in toluene for 96 hours. The reaction was cooled and concentrated in vacuo. The residue was partitioned between saturated aqueous sodium bicarbonate and dichloromethane. The organic phase was dried over sodium sulfate and concentrated in vacuo and the residue was purified by chromatography on silica gel to afford the title compound. MH+ 388.

DESCRIPTION 22

3,N-Dimethyl-N-(2-piperazin-1-yl-ethyl)-benzene Sulfonamide (D22)

A solution of D21 (6 g, 16 mmol) in ethanol (50 ml) and acetic acid (50 ml) was hydrogenated over palladium on charcoal catalyst (600 mg) for 72 hours. The catalyst was recovered by filtration, washed with ethanol and the combined organics concentrated in vacuo to afford the title compound. MH+ 298.

DESCRIPTION 23

{2-[4-(1H-Benzimidazol-2-yl)-piperazin-1-yl]-ethyl}-methyl-amine Hydrochloride Salt (D23)

A mixture of 2-piperazin-1-yl-1H-benzimidazole (0.7 g, 3.47 mmol), sodium iodide (0.79 g, 5.26 mmol), dry potassium carbonate (0.48 g, 3.5 mmol) and (2-chloro-ethyl)-methyl-amine hydrochloride salt (0.46 g, 3.56 mmol) in dimethylformamide was heated at 100° C. for 1H under argon. Afterwards, a further amount of dry potassium carbonate (0.48 g, 3.5 mmol) and 1-chloro-2-(methylamino) ethane (0.46 g, 3.56 mmol) was added and the reaction mixture was heated at 100° C. for another 4 h. The mixture was cooled to room temperature, the solid was filtered off, washed with dichloromethane. The combined filtrates were evaporated, the residue was partially dissolved in dichloromethane (70 ml), the solid was collected by filtration, washed with dichloromethane (2×10 ml) and dried to give the product as an hydrochloride salt; yellowish solid (0.5 g, 49%): MH+=260.

EXAMPLE 1

N-(2-(4-(1H-Benzimidazol-2-yl)-piperidin-1-yl) ethyl)-3,N-dimethyl Benzene Sulfonamide (E1)

To a solution of D1 (192 mg, 0.5 mmol) in acetonitrile was added D14 (100 mg, 0.5 mmol), potassium carbonate (140 mg, 1.0 mmol) and catalytic sodium iodide (5 mg). The reaction mixture was heated to reflux for 18 hours then cooled and concentrated in vacuo. After partitioning between saturated aqueous sodium bicarbonate and dichloromethane the organic phase was dried over sodium sulfate and concentrated in vacuo. The residue was purified by chromatography on silica gel to afford the title compound (49 mg, 24%).

1H NMR (CDCl$_3$) 7.58 (3H, m), 7.38 (2H, m), 7.19 (2H, m) 3.15 (2H, t, 6.7 Hz), 2.90 (3H, m), 2.80 (3H, s), 2.56 (2H, t, 6.7 Hz), 2.43 (3H, s), 2.15 (4H, m), 1.89 (2H, m). MH+ 413.

EXAMPLES E2–21 SHOWN IN TABLE 1 WERE PREPARED USING A PROCEDURE SIMILAR TO THAT DESCRIBED IN EXAMPLE E1 USING TOLUENE-3-SULFONIC ACID 2-(METHYL-(TOLUENE-3-SULFONYL)-AMINO)-ETHYL ESTER (D1) AND A 4-SUBSTITUTED PIPEIDINE.

TABLE 1

| Example | R | MH+ |
|---|---|---|
| E2 | Phenyl | 373 |
| E3 | Benzyl | 387 |
| E4 | 1H-Indol-3-yl | 412 |
| E5 | 5-Methyl-1H-indol-3-yl | 426 |
| E6 | 5-Methoxy-1H-indol-3-yl | 442 |
| E7 | 5-Carbomethoxy-1H-indol-3-yl | 470 |
| E8 | 7-Methyl-1H-indol-3-yl | 426 |
| E9 | 4-Methyl-1H-benzimidazol-2-yl | 427 |
| E10 | 5-Methyl-1H-benzimidazol-2-yl | 427 |
| E11 | 5-Hydroxy-1H-benzimidazol-2-yl | 429 |
| E12 | 5-Fluoro-1H-benzimidazol-2-yl | 431 |
| E13 | Benzoxazol-2-yl | 414 |
| E14 | Benzothiazol-2-yl | 430 |
| E15 | Naphthalen-1-yl | 423 |
| E16 | Naphthaten-2-yl | 423 |
| E17 | 5-Chloro-1H-benzimidazol-2-yl | 447/449 |
| E18 | 5-Fluoro-benzoxazol-2-yl | 432 |
| E19 | 6-Fluoro-benzoxazol-2-yl | 432 |
| E20 | 6-Chloro, 5-fluoro-1H-benzimidazol-2-yl | 465/467 |
| E21 | 1H-Indol-2-yl | 412 |

EXAMPLES E22–25 SHOWN IN TABLE 2 WERE PREPARED USING A PROCEDURE SIMILAR TO THAT DESCRIBED IN EXAMPLE E1 USING 4-FLUOROBENZENESULFONIC ACID 2-((4-FLUOROBENZENESULFONYL)-METHYL-AMINO)-ETHYL ESTER (D2) AND A 4-SUBSTITUTED PIPERIDINE.

TABLE 2

| Example | R | MH+ |
|---|---|---|
| E22 | Phenoxy | 393 |
| E23 | Benzoyl | 405 |
| E24 | 2-oxo-2,3 dihydro benzimidazol-1-yl | 433 |
| E25 | 1H-Indol-3-yl | 416 |

EXAMPLE 26

3,4 Dichloro-N2-(4-(1H-indol-3-yl)piperidin-1-yl)-ethyl)-N-methyl-benzene Sulfonamide (E26)

The title compound was prepared using the procedure described in Example 1 using 3,4-dichlorobenzenesulfonic acid 2-((3,4dichlorobenzenesulfonyl)-methyl-amino)-ethyl ester (D3) and a 4-(1H-indol-3-yl)-piperidine. MH+ 467.

EXAMPLES E27 AND E28 SHOWN IN TABLE 3 WERE PREPARED USING 2,4,5-TRICHLOROBENZENE SULFONIC ACID 2-(METHYL-(2,4,5-TRICHLOROBENZENESULFONYL)-AMINO)-ETHYL ESTER (D4) AND A SUBSTITUTED PIPERIDINE.

TABLE 3

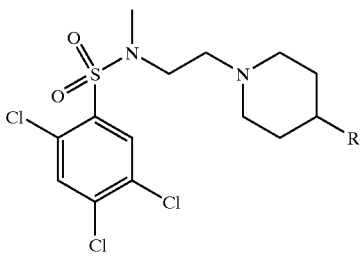

| Example | R | MH+ |
|---------|---|-----|
| E27 | 2-amino-benzoyl | 504/506/508/510 |
| E28 | 4-(5-fluoro-1H-benzimidazol-2-yl) | 519/521/523/525 |

EXAMPLE 29

2,4,5-Trichloro-N-ethyl-(2-(4-(5-fluoro-1H-benzimidazol-2-yl)-piperidin-1-yl-ethyl)-benzene Sulfonamide (E29)

The title compound was prepared using the procedure described in Example 1 using D6 and 4-(5-fluoro-1H-benzimidazol-2-yl)piperidine (D17). MH+ 533/535/537/539.

EXAMPLE 30

2,4,5-Trichloro-N-(2-(4-(5-Fluoro-1H-benzimidazol-2-yl)piperidin-1-yl)-ethyl)-N-isopropyl Benzene Sulfonamide (E30)

The title compound was prepared using the procedure described in Example 1 using D7 and 4-(5-fluoro-1H-benzimidazol-2-yl)piperidine (D17). MH+ 547/549/551/553.

EXAMPLE 31

4-Chloro-2,5-dimethyl-N-(2-(4-(5fluoro-1H-benzimidazol-2-yl)-piperidin-1-yl)-ethyl)-N-isopropyl Benzene Sulfonamide (E31)

The title compound was prepared using the procedure described in Example 1 using D8 and 4-(5-fluoro-1H-benzimidazol-2-yl)piperidine (D17). MH+ 507/509.

EXAMPLE 32

N-(2-(4-(1H-Benzimidazol-2-yl)-piperazin-1-yl)-ethyl)-2,4,5-trichloro-N-isopropyl-benzene-sulfonamide (E32)

The title compound was prepared using the procedure described in Example 1 using D7 and 1-(1H-benzimidazol-2-yl)piperazine. MH+ 530/532/534/536.

EXAMPLE 33

3,N-Dimethyl-N-(2-(4-(2-methyl-1H-indol-3-yl)-3,6 dihydro-2H-pyridin-1-yl)-ethyl)-benzene Sulfonamide (E33)

The title compound was prepared using the procedure described in Example 1 using toluene-3-sulfonic acid 2-(methyl-(toluene-3-sulfonyl)-amino)-ethyl ester (D1) and 2-methyl-3-(1,2,3,6-tetrahydro-pyridin-4-yl)-1H indole. MH+ 424.

EXAMPLE 34

4-Fluoro-(N-(2-(4-(2-oxo-2,3-dihydro-benzimidazol-1-yl)3,6-dihydro-2H-pyridin-1-yl)-ethyl)-benzene Sulfonamide (E34)

The title compound was prepared using the procedure described in Example 1 using 4-fluorobenzenesulfonic acid 2-((4-fluorobenzenesulfonyl)-methyl-amino)-ethyl ester (D2) and 1-(1,2,3,6-tetralydro-pyridin yl)-1,3-dihydro benzimidazol-2-one. MH+ 431.

EXAMPLE 35

2,3,4-Trichloro-N(2-(4-(5-fluoro-1H-benzimidazol-2-yl)-piperidin-1-yl)-ethyl-N-methyl-benzene-sulfonamide (E35)

The title compound was prepared using the procedure described in Example 1 using 2,3,4-Trichloro-N-(2-chloroethyl)-N-methyl benzene sulfonamide (D9) and 4-(5-fluoro 1H benzimidazol-2-yl)piperidine (D17). MH+ 519/521/523/525.

EXAMPLE 36

2,5-Dibromo-N-2-(4-(5-fluoro-1H-benzimidazol-2-yl)-piperidin-1-yl)ethyl-N-methyl-benzene-sulfonamide (E36)

The title compound was prepared using the procedure described in Example 1 using 2,5-Dibromo-N-(2-chloroethyl)-N-methyl benzene sulfonamide (D10) and 4-(5-fluoro 1H benzimidazol-2-yl)piperidine (D17). MH+ 5731575/577.

EXAMPLE 37

2,4-Dichloro-N-(2-(4-(5-Fluoro-1H-benzimidazol-2-yl)-piperidin-1-yl)ethyl-5,N-dimethyl-benzene-sulfonamide (E37)

The title compound was prepared using the procedure described in Example 1 using 2,4dichloro-N-(2-chloroethyl)-N-methyl benzene sulfonamide (D11) and 4-(5-fluoro 1H benzimidazol-2-yl)piperidine (D17). MH+ 499/501/503.

EXAMPLE 38

4,5-Dichloro-N-(2-(4-(5-fluoro-1H-benzimidazol-2-yl)-piperidin-1-yl)-ethyl)-N-methyl-2-trifluoromethyl-benzenesulfonamide (E38)

The title compound was prepared using the procedure described in Example 1 using 4,5-dichloro-N-(2-chloroethyl)-N-methyl-2-trifluoromethyl-benzenesulfonamide (D12) and 4-(5-fluoro 1H benzimidazol-2-yl)piperidine (D17). MH+ 581/583/585.

EXAMPLE 39

2-Chloro-4-fluoro-N-(2-(4-(5-fluoro-1H-benzimidazol-2-yl)-piperidin-1-yl)-ethyl-N-methyl-benzene-sulfonamide (E39)

The title compound was prepared using the procedure described in Example 1 using 2-chloro-4 fluoro-N-(2-chloroethyl)-N-methyl benzene sulfonamide (D13) and 4-(5-fluoro 1H benzimidazol-2-yl)piperidine (D17). MH+ 469/470.

EXAMPLE 40

N-(2-(4-(1H-Benzimidazol-2-yl)-piperazin-1-yl)-ethyl)-3,N-dimethyl Benzene Sulfonamide (E40)

A solution of D22 (0.50 g, 1.6 mmol) and 2-chloro 1H benzimidazole (0.25 g, 1.6 mmol) in toluene were heated at reflux for 14 hours. On cooling, the solvent was removed in vacuo and the residue partitioned between saturated aqueous sodium bicarbonate and dichloromethane. The organics were dried over sodium sulfate and concentrated in vacuo. The residue was purified by chromatography on silica gel to afford the title compound (150 mg, 22%) MH+ 414.

EXAMPLES E41–47 SHOWN IN TABLE 4 WERE PREPARED USING THE PROCEDURE SIMILAR TO THAT DESCRIBED IN EXAMPLE E1 USING TOLUENE-3-SULFONIC ACID 2-(METHYL-(TOLUENE-3-SULFONYL)-AMINO)-ETHYL ESTER (D1) AND A N-SUBSTITUTED PIPERAZINE.

TABLE 4

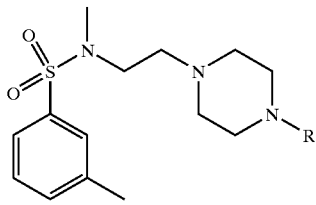

| Example | R | MH+ |
|---|---|---|
| E41 | 2-Chlorophenyl | 408/410 |
| E42 | 3-Trifluoromethylphenyl | 442 |
| E43 | Pyrimidin-2-yl | 376 |
| E44 | 5-Ethylpyrimidin-2-yl | 404 |
| E45 | 6-Chlorobenzothiazol-2-yl | 465/467 |
| E46 | Benzoxazol-2-yl | 415 |
| E47 | 6-Chloroquinolin-4-yl | 460 |

EXAMPLE 48

N-2-(4-(1H-Benzimidazol-2-yl)-piperazin-1-yl)-ethyl)-2,4,5-trichloro-N-methyl-benzenesulfonamide (E48)

The title compound was prepared using the procedure described on Example 1 using 2,4,5-Trichlorobenzenesulfonic acid 2-(methyl-(2,4,5-trichlorobenzenesulfonyl)-amino)-ethyl ester (D4) and 1-(1H benzimidazol-2-yl) piperazine. MH+ 502/504/506/508.

EXAMPLE 49

2,4,5-Trichloro-N-(2-(4-(5-fluoro-1H-benzimidazol-2-yl)piperazin-1-yl)-ethyl)-N-methyl benzene sulfonamide (E49)

The title compound was prepared using the procedure described in Example 1 using 2,4,5-Trichlorobenzenesulfonic acid 2-(methyl-(2,4,5-trichlorobenzenesulfonyl)-amino)-ethyl ester (D4) and 1-(5-fluoro-1H benzimidazol-2-yl) piperazine. MH+ 520/522/524/526.

EXAMPLE 50

4-Fluoro-N-(2-(4-(2-methoxyphenyl)-piperazin-1-yl)-ethyl)-N-methyl Benzene Sulfonamide (E50)

The title compound was prepared using the procedure described in Example 1 using 4-fluorobenzenesulfonic acid 2-((4-fluorobenzenesulfonyl)-methyl-amino)-ethyl ester (D2) and 4-(2-methoxyphenyl)-piperazine. MH+ 408.

EXAMPLE 51

N-{2-[4-(1H-Benzimidazol-2-yl)-piperazin-1-yl]-ethyl}-2,4-dichloro-5,N-dimethyl-benzenesulfonamide (E51)

A mixture of 2,4-dichloro-5-methylbenzenesulphonyl chloride (81 mg, 0.31 mmol), {2-[4-(1H-Benzimidazol-2-yl)-piperazin-1-yl]-ethyl}-methyl-amine hydrochloride salt (D23) (80 mg, 0.31 mmol) and pyridine (0.5 ml) in dry dichloromethane (5 ml) was stirred at room temperature for 17 h. The mixture was then diluted with dichloromethane (30 ml), washed with aqueous sodium bicarbonate (1×10 ml) and dried.(MgSO$_4$). The solvent was evaporated and the residue was co-evaporated with toluene (5 ml). Column chromatography of the residue (eluting with methanol-dichloromethane gradient) gave the product as a yellowish solid (25 mg, 17%); MS: m/z (MH$^+$)=482.

EXAMPLES E52–58 SHOWN IN TABLE 5 WERE PREPARED USING A PROCEDURE SIMILAR TO THAT DESCRIBED IN EXAMPLE E51 USING D23 AND A SUBSTITUTED AROMATIC SULFONYL CHLORIDE

TABLE 5

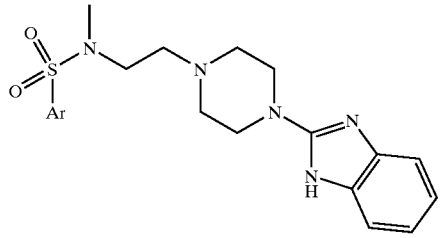

| Example | Ar | MH+ |
|---|---|---|
| E52 | 4-Bromo-5-chloro thiophen-2-yl | 518/520/522 |
| E53 | 2,4 dichloro 5-methylphenyl | 482/484/486 |
| E54 | 4-bromo 2,5 difluorophenyl | 514/516 |
| E55 | 5-chloro 2-methoxyphenyl | 464/466 |
| E56 | 2-ethyl 4-bromophenyl | 506/508 |
| E57 | 4-bromo 2-trifluoromethoxyphenyl | 562/564 |
| E58 | 2-chloro 4-fluorophenyl | 452/454 |

Pharmacological Testing

[$^3$H]-5-Carboxamidotryptamine Binding to Human 5-HT$_7$ Receptor Clones Expressed in 293 Cells in vitro The affinity of the compounds of this invention for the 5-HT$_7$ receptor binding site can be determined by methods described in WO 97/29097. All compounds tested had a pKi in the range 6.2–9.0. Examples E28–31, E37 and E38 had a pKi>8.5.

What is claimed is:

1. A compound of formula (I) or a pharmaceutically acceptable salt thereof:

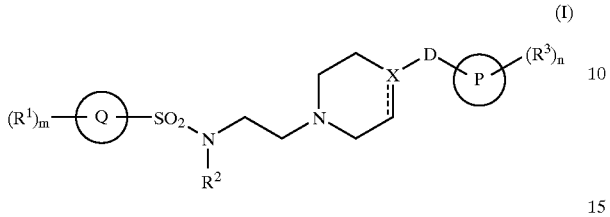

(I)

wherein:
Q is phenyl or thienyl;
$R^1$ is halogen, hydroxy, $C_{1-6}$alkyl, $CF_3$, $OCF_3$ or $C_{1-6}$alkoxy;
m is 0, 1, 2 or 3;
$R^2$ is $C_{1-4}$alkyl;
X is carbon or CH,
=== is a single bond when X is CH or
=== is a double bond when X is carbon,
D is a single bond, C=O, O or $CH_2$ subject to the proviso that when X is nitrogen then D is not oxygen;
P is a 5 or 6 membered heteroaryl ring containing 1 to 3 heteroatoms selected from oxygen, nitrogen and sulphur, or a benzofused heteroaryl ring containing 1 to 3 heteroatoms selected from oxygen, nitrogen and sulphur;
$R^3$ is $C_{1-6}$alkyl optionally substituted by $NR^4R^5$, aryl, aryl$C_{1-6}$alkyl, $C_{1-6}$alkoxy, $C_{1-6}$alkylthio, cyano, hydroxy, nitro, halogen, $CF_3$, $C_2F_5$, $NR^4R^5$, $CONR^4R^5$, $NR^4COR^5$, $S(O)_pNR^4R^5$, CHO, $OCF_3$, $SCF_3$, $CH_2OR^6$, $CO_2R^6$ or $COR^6$ where p is 0, 1 or 2 and $R^4$, $R^5$ and $R^6$ are independently hydrogen, $C_{1-6}$alkyl, aryl or aryl$C_{1-6}$alkyl;
n is 0, 1, 2 or 3.

2. A compound according to claim 1 in which Q is phenyl.
3. A compound according to claim 1 in which $R^2$ is methyl or isopropyl.
4. A compound according to claim 1 in which X is nitrogen or a CH group.
5. A compound according to claim 1 in which P is benzimidazol-2-yl.
6. A compound according to claim 1 which is
N2-(4-(1H-Benzimidazol-2-yl)-piperidin-1-yl)-ethyl)-3,N-dimethyl benzene sulfonamide;
3,4-Dichloro-N-(2-(4-(1H-indol-3-yl)-piperidin-1-yl)-ethyl)-N-methyl-benzene sulfonamide;
2,4,5-Trichloro-N-ethyl-(2-(4-(5-fluoro-1H-benzimidazol-2-yl)-piperidin-1-yl)-ethyl)-benzene sulfonamide;
2,4,5-Trichloro-N-(2-(4-(5-fluoro-1H-benzimidazol-2-yl)-piperidin-1-yl)-ethyl)-N-isopropyl benzene sulfonamide;
4-Chloro-2,5-dimethyl-N-(2-(4-(5-fluoro-1H-benzimidazol-2-yl)-piperidin-1-yl)-ethyl)-N-isopropyl benzene sulfonamide;
2,3,4-Trichloro-N-(2-(4-(5-fluoro-1H-benzimidazol-2-yl)-piperidin-1-yl)-ethyl-N-methyl-benzene-sulfonamide;
2,5-Dibromo-N-(2-(4-(5-fluoro-1H-benzimidazol-2-yl)-piperidin-1-yl)-ethyl-N-methyl-benzene-sulfonamide;
2,4-Dichloro-N-(2-(4-(5-fluoro-1H-benzimidazol-2-yl)-piperidin-1-yl)-ethyl-5,N-dimethyl-benzene-sulfonamide;
4,5-Dichloro-N-(2-(4-(5-fluoro-1H-benzimidazol-2-yl)-piperidin-1-yl)-ethyl)N-methyl-2-trifluorometh benzenesulfonamide; and
2-Chloro-4-fluoro-N-(2-(4-(5-fluoro-1H-benzimidazol-2-yl)-piperidin-1-yl)-ethyl)-N-methyl-benzene-sulfonamide;

or a pharmaceutically acceptable salt thereof.

7. A process for the preparation of a compound of formula (I) or a pharmaceutically acceptable salt thereof, which process comprises coupling a compound of formula (II):

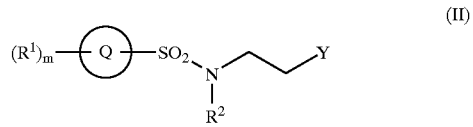

(II)

in which Q, $R^1$, $R^2$ and m are as defined in formula (I) and Y is a leaving group with a compound of formula (III):

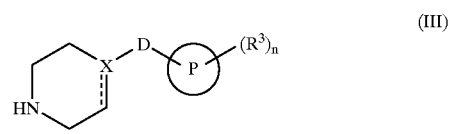

(III)

in which === X, D, P, n and $R^3$ are as defined in formula (I);

and optionally thereafter if appropriate:
    removing any protecting groups;
    forming a pharmaceutically acceptable salt.

8. A pharmaceutical composition which comprises a compound according to claim 1 and a pharmaceutically acceptable carrier or excipient.

9. A method of treating depression, or migraine comprising administering to a subject a safe and effective amount of a compound according to claim 1.

* * * * *